US007324679B2

(12) United States Patent
Moriyama (10) Patent No.: US 7,324,679 B2
(45) Date of Patent: Jan. 29, 2008

(54) MEDICAL IMAGE RADIOGRAPHING SYSTEM AND PORTABLE RADIOGRAPHING INFORMATION APPARATUS

(75) Inventor: Naoto Moriyama, Hachioji (JP)

(73) Assignee: Konica Minolta Holdings, Inc. (JP)

( * ) Notice: Subject to any disclaimer, the term of this patent is extended or adjusted under 35 U.S.C. 154(b) by 616 days.

(21) Appl. No.: 10/694,653

(22) Filed: Oct. 27, 2003

(65) Prior Publication Data

US 2004/0089710 A1 May 13, 2004

(30) Foreign Application Priority Data

Oct. 31, 2002 (JP) ............................. 2002-317451

(51) Int. Cl.
*G06K 9/00* (2006.01)

(52) U.S. Cl. ....................... 382/132; 382/128; 382/131; 382/305; 707/104; 707/204; 250/584

(58) Field of Classification Search ................ 382/132, 382/128, 131, 305; 707/204, 104; 250/584
See application file for complete search history.

(56) References Cited

U.S. PATENT DOCUMENTS

| 5,051,849 | A | * | 9/1991 | Fukushima et al. ........... 360/69 |
| 5,140,518 | A | | 8/1992 | Ema |
| 5,282,236 | A | | 1/1994 | Hayes et al. |
| 5,329,445 | A | * | 7/1994 | Mukai ........................ 382/128 |
| 5,334,851 | A | | 8/1994 | Good et al. |
| 5,865,745 | A | | 2/1999 | Schmitt et al. |
| 6,271,536 | B1 | | 8/2001 | Buytaert et al. |
| 6,379,044 | B1 | * | 4/2002 | Vastenaeken et al. ........ 378/207 |
| 6,405,165 | B1 | * | 6/2002 | Blum et al. .................. 704/235 |
| 6,678,703 | B2 | * | 1/2004 | Rothschild et al. .......... 707/201 |
| 6,920,465 | B2 | * | 7/2005 | Motoki ..................... 707/104.1 |
| 6,954,767 | B1 | * | 10/2005 | Kanada ...................... 707/204 |
| 7,092,970 | B2 | * | 8/2006 | Shiibashi et al. ......... 707/104.1 |
| 2004/0086164 | A1 | * | 5/2004 | Moriyama et al. ........... 382/131 |

* cited by examiner

*Primary Examiner*—Samir Ahmed
*Assistant Examiner*—Nancy Bitar
(74) *Attorney, Agent, or Firm*—Cantor Colburn LLP (57) ABSTRACT

A medical image radiographing system has a medical image reading apparatus to read out identification information of a cassette and a medical image from the cassette recording the medical image radiographed according to radiographing order information, a portable radiographing information apparatus having a correspondence setting section to set correspondence of the identification information of the cassette to the radiographing order information for radiographing using the cassette, and a judging section to judge whether or not the cassette is usable for next radiographing. The correspondence setting section prohibits the setting of the correspondence of the identification information of the cassette, which is judged by the judging section to be nonusable for the next radiographing, to the radiographing order information.

12 Claims, 7 Drawing Sheets

| ORDER ID | PATIENT INFORMATION | | | | | RADIOGRAPHING INFORMATION | | | | IMAGE PROCESSING CONDITION | OUTPUT CONDITION | |
|---|---|---|---|---|---|---|---|---|---|---|---|---|
| | PATIENT ID | PATIENT NAME | SEX | AGE | ... | RADIOGRAPHING CONDITION | CASSETTE ID | ... | | | | |
| 0001 | AA-001 | HANAKO SUZUKI | FEMALE | 45 | ... | CHEST FRONT | AB01 | ... | CONTRAST +1 | FILM SIZE 14x14 | ... |
| 0002 | AA-001 | HANAKO SUZUKI | FEMALE | 45 | ... | CHEST SIDE | AB02 | ... | CONTRAST +1 | FILM SIZE 14x14 | ... |
| 0003 | AA-001 | HANAKO SUZUKI | FEMALE | 45 | ... | ABDOMEN FRONT | AB03 | ... | CONTRAST +1 | FILM SIZE 14x14 | ... |
| 0004 | AB-001 | TARO YAMADA | MALE | 50 | ... | SKULL FRONT | CD02 | ... | — | — | ... |
| 0005 | AB-001 | TARO YAMADA | MALE | 50 | ... | SKULL SIDE | CD05 | ... | — | — | ... |
| ... | ... | ... | ... | ... | ... | ... | ... | ... | ... | ... | ... |

| RADIOGRAPHING ORDER INFORMATION | REGISTERED CASSETTE | MEDICAL IMAGE | USABLE/ NONUSABLE |
|---|---|---|---|
| ORDER 1 | AA01 | IMAGE A | USABLE |
| ORDER 2 | AA02 | IMAGE B | USABLE |
| ORDER 3 | AB01 | — | NONUSABLE |
| ORDER 4 | AB03 | IMAGE C | USABLE |
| .... | .... | .... | .... |

MEDICAL IMAGE RADIOGRAPHING SYSTEM AND PORTABLE RADIOGRAPHING INFORMATION APPARATUS

BACKGROUND OF THE INVENTION

1. Field of the Invention

The present invention relates to a medical image radiographing system and a portable radiographing information apparatus.

2. Description of Related Art

In a field of medicine, a medical image radiographing (or tomographing) system having a computed tomographing apparatus (hereinafter, named "computed tomography (CT)"), a computed radiation image radiographing apparatus (hereinafter, named "computed radiography (CR)"), a nuclear magnetic resonance imaging apparatus (hereinafter, named "magnetic resonance imaging (MRI)") or the like has been used. In this medical image radiographing system, a patient denoting a subject is radiographed, and a radiographed medical image is obtained as digital image data.

In the CR, a photostimulable phosphor plate with a photostimulable phosphor layer formed on a support member is in use. In radiographing, radiations transmitted through a subject are absorbed in the photostimulable phosphor layer, and an amount of radiation energy corresponding to the radiation transmittance of each part of the subject is accumulated in the photostimulable phosphor layer to form a latent image in the photostimulable phosphor layer. Thereafter, the photostimulable phosphor layer is scanned by excitation light such as laser light or the like to release the accumulated radiation energy as fluorescence, and the fluorescence is photoelectrically converted to an image signal. The image signal is read out to obtain a medical image.

The medical image radiographing-system described above is classified into a fixed type system and a movable type system.

In the fixed type medical image radiographing system, a radiographing and reading apparatus having the photostimulable phosphor plate is fixedly arranged in a radiographing room to perform the radiographing and reading-out. In this system, a radiographed image of the radiographing can be read out from the photostimulable phosphor plate as data of a digital image in succession to the radiographing.

In the movable type medical image radiographing system, because patients cannot go to a room having a fixed type radiographing apparatus when they are in a just-after-medical-operation condition, seriously injured and/or the like, the radiographing of the patients is performed at visited patient's positions by using both a movable radiographing apparatus (hereinafter, named a portable radiographing apparatus) applied to a doctor's round of visits and a cassette accommodating the photostimulable phosphor plate. After the radiographing, a radiographed image is read out from the cassette by using a reader privately used for the cassette, and data of a digital image is obtained.

In this movable type medical image radiographing system, an examination operator generally performs the radiographing according to following procedure.

(1) In a system (hereinafter, named "hospital information system (HIS)") managing information obtained in a hospital or a system (hereinafter, named "radiology information system (RIS)") managing information obtained in a radiation treatment section, radiographing order information prepared in response to each order of a doctor is printed out on an order sheet. The radiographing order information includes patient information of a radiographed patient such as a name, a sex and the like and radiographing information such as a radiographic part of the patient, a radiographing method and the like. Therefore, the radiographing order information indicates how a specified patient is radiographed.

(2) The portable radiographing apparatus and the cassette are carried to each hospital room in which one patient stays.

(3) The patient to be radiographed and the radiographic part of the patient are specified according to the radiographing order information printed out on the order sheet, and the radiographing is performed according to the radiographing order information by using the radiographing apparatus and the cassette.

(4) After the radiographing, the cassette having a medical image of the patient is attached to the reader privately used for the cassette, and the radiographed medical image is read out. Thereafter the radiographing order information corresponding to the read-out medical image is identified.

In recent years, to read out the medical image recorded in each cassette, the cassette is specified by attaching identification information expressed by a barcode to the surface of the cassette and reading out the barcode by a barcode reader.

Meanwhile, to prevent the barcode reader from reading out twice the barcode as an error case, a technique to prevent the reread-out of the barcode for a predetermined period of time after the read-out of the barcode has been disclosed in Unexamined Japanese Patent Publication (Tokkai) 11-53465 (pp. 5-8 and FIG. 1, and hereinafter named a patent document).

However, in the radiographing method described above, the radiographing order information is printed out on a paper medium such as the order sheet for each radiographing order. Therefore, when there is/are a or a plurality of radiographing orders for one patient, the handling of one or more pieces of radiographing order information for the patient becomes troublesome, and there is a case where the cassette and the radiographing order information used for the radiographing of the patient cannot be specified. Further the radiographing order information includes image processing conditions of the radiographed medical image, and the image processing appropriate to the radiographic part of the patient is performed for the medical image read out from the cassette according to the radiographing order information after the radiographing. Therefore, when the correspondence of a medical image to radiographing order information different from the correspondence of the medical image to proper radiographing order information really corresponding to the medical image is erroneously set, the image processing cannot be appropriately performed for the medical image, and there is a possibility that the accuracy in diagnosis for the patient is lowered. Accordingly, pieces of radiographing order information require to be handled accurately and safely.

Further, each cassette can be used many times by erasing the radiographed medical image of the cassette after the read-out of the medical image, and it is impossible to judge whether or not the cassette records the medical image. Therefore, there is a possibility that the cassette is erroneously used for next radiographing when the read-out of the medical image from the cassette is not completed.

SUMMARY OF THE INVENTION

In order to solve the above problem, an object of the present invention is to provide a medical image radiographing system and a portable radiographing information apparatus, in which the easy and accurate handling of radiographing order information is secured and the safety of the medical image is secured by preventing the duplicated radiographing from being performed for one cassette.

In order to accomplish the above-mentioned object, in accordance with the first aspect of the present invention, a medical image radiographing system, comprises:

a medical image reading apparatus to read out identification information of a cassette and a medical image from the cassette recording the medical image radiographed according to radiographing order information;

a portable radiographing information apparatus having a correspondence setting section to set correspondence of the identification information of the cassette to the radiographing order information for radiographing using the cassette; and a judging section to judge whether or not the cassette is usable for next radiographing, wherein the correspondence setting section prohibits th setting of the correspondence of the identification information of the cassette, which is judged by the judging section to be nonusable for the next radiographing, to the radiographing order information.

In the first aspect of the present invention, because the portable radiographing information apparatus sets the correspondence of the identification information of the cassette used for the radiographing to the radiographing order information used for the cassette, the easiness and accuracy of the handling of the radiographing order information can be secured. Further, the judging section judges whether or not the cassette used for the radiographing is usable for the next radiographing, and the portable radiographing information apparatus prohibits the setting of the correspondence of the identification information of the cassette judged to be nonusable for the next radiographing to the radiographing order information. Accordingly, the duplicating radiographing for one cassette can be prevented, and the safety of the radiographed medical image can be secured.

Preferably, the medical image radiographing system further comprises:

a control apparatus to control the medical image reading apparatus to obtain the identification information and the medical image of the cassette, the control apparatus comprising:
the judging section; and
a judging result transmitting section to transmit a judging result obtained by the judging section to the portable radiographing information apparatus, wherein the correspondence setting section of the portable radiographing information apparatus prohibits the setting of the correspondence according to the judging result transmitted from the judging result transmitting section.

Preferably, the medical image reading apparatus sets the correspondence of the identification information of the cassette to the medical image read out from the cassette, and the control apparatus further comprises:

an image correspondence setting section to set the correspondence of the medical image to the radiographing order information according to both the identification information of the cassette and the radiographing order information of which the correspondence to each other is set by the correspondence setting section and both the identification information of the cassette and the medical image of which the correspondence to each other is set by the medical image reading apparatus.

Preferably, the portable radiographing information apparatus further comprises:

a radiographing order receiving section to receive one or more pieces of radiographing order information;

a storing section to store the one or more pieces of radiographing order information received by the radiographing order receiving section;

an input section to input the identification information of the cassette used for radiographing in; and a radiographing order transmitting section to transmit the identification information of the cassette and the radiographing order information, of which the correspondence to each other is set by the correspondence setting section, to the control apparatus after the radiographing, wherein the correspondence setting section of the portable radiographing information apparatus sets the correspondence of the identification information of the cassette inputted by the input section to one piece of radiographing order information which is selected from the one or more pieces of radiographing order information stored by the storing section and which relates to the radiographing using the cassette, and wherein the judging section judges whether or not the cassette is usable for the next radiographing, according to both the identification information of the cassette and the radiographing order information transmitted by the radiographing order transmitting section and both the identification information of the cassette and the medical image obtained by the medical image reading apparatus.

It will be appreciated that each of the correspondence setting section, the radiographing order (information) receiving section, the storing section, the input section, the radiographing order transmitting section and the like may comprise a single unit or a plurality of units. Further, it will be appreciated that one unit or units are arranged in common in two sections or more selected from the correspondence setting section, the radiographing order receiving section, the storing section, the input section, the radiographing order transmitting section and the like. As an example that one unit or units are arranged in common in two sections or more selected from the correspondence setting section, the radiographing order (information) receiving section, the storing section, the input section and the radiographing order transmitting section, the radiographing order receiving section and the radiographing order transmitting section have one data transceiver as a common unit. Further, the correspondence setting section has a central processing unit (CPU) having an internal memory, and the storing section denotes the internal memory of the CPU.

Preferably, the control apparatus and the portable radiographing information apparatus are connected with each other through a network, and the medical image reading apparatus and the control apparatus are connected with each other through a wire.

Preferably, the control apparatus, the portable radiographing information apparatus and the medical image reading apparatus are connected with one another through a network.

Preferably, the portable radiographing information apparatus further comprises a warning section to warn that the cassette is nonusable when the identification information of the cassette inputted by the input section agrees with the identification information of the cassette judged to be nonusable for the next radiographing, according to a judging result of the judging section.

Preferably, the medical image reading apparatus sets the correspondence of the identification information of the cassette to the medical image read out from the cassette, and the system further comprises:

an image correspondence setting section to set the correspondence of the medical image to the radiographing order information according to both the identification information of the cassette and the radiographing order information of which the correspondence to each other is set by the correspondence setting section and both the identification information of the cassette and the medical image of which the correspondence to each other is set by the medical image reading apparatus.

In accordance with the second aspect of the present invention, a portable radiographing information apparatus is connected with a medical image reading apparatus to read out identification information of a cassette and a medical image from the cassette recording the medical image radiographed according to radiographing order information, and the portable radiographing information apparatus comprises:

a radiographing order information receiving section to receive one or more pieces of radiographing order information;

a storing section to store the one or more pieces of radiographing order information received by the radiographing order information receiving section;

an input section to input the identification information of the cassette used for radiographing in;

a correspondence setting section to set correspondence of the identification information of the cassette inputted by the input section to one piece of radiographing order information which is selected from the one or more pieces of radiographing order information stored by the storing section and which relates to the radiographing using the cassette; and a radiographing order transmitting section to transmit the identification information of the cassette and the radiographing order information of which the correspondence to each other is set by the correspondence setting section, wherein the correspondence setting section prohibits the setting of the correspondence of the piece of identification information of the cassette, which is judged to be nonusable for next radiographing, to the radiographing order information of the cassette used for the next radiographing.

In the second aspect of the present invention, the same effects as those in the first aspect can be obtained.

Preferably, the portable radiographing information apparatus further comprises a warning section to warn that the cassette is nonusable when the identification information of the cassette inputted by the input section agrees with the identification information of the cassette judged to be nonusable for the next radiographing.

Preferably, the portable radiographing information apparatus is connected with the medical image reading apparatus through a control apparatus.

Preferably, the portable radiographing information apparatus is connected with the medical image reading apparatus through a network.

BRIEF DESCRIPTION OF THE DRAWINGS

The present invention will become more fully understood from the detailed description given hereinbelow and the accompanying drawing which are given by way of illustration only, and thus are not intended as a definition of the limits of the present invention, and wherein.

PREFERRED EMBODIMENTS OF THE INVENTION

Hereinafter, the embodiment of the present invention will be explained with reference to the drawings.

The configuration will be initially described.

Figure 1:
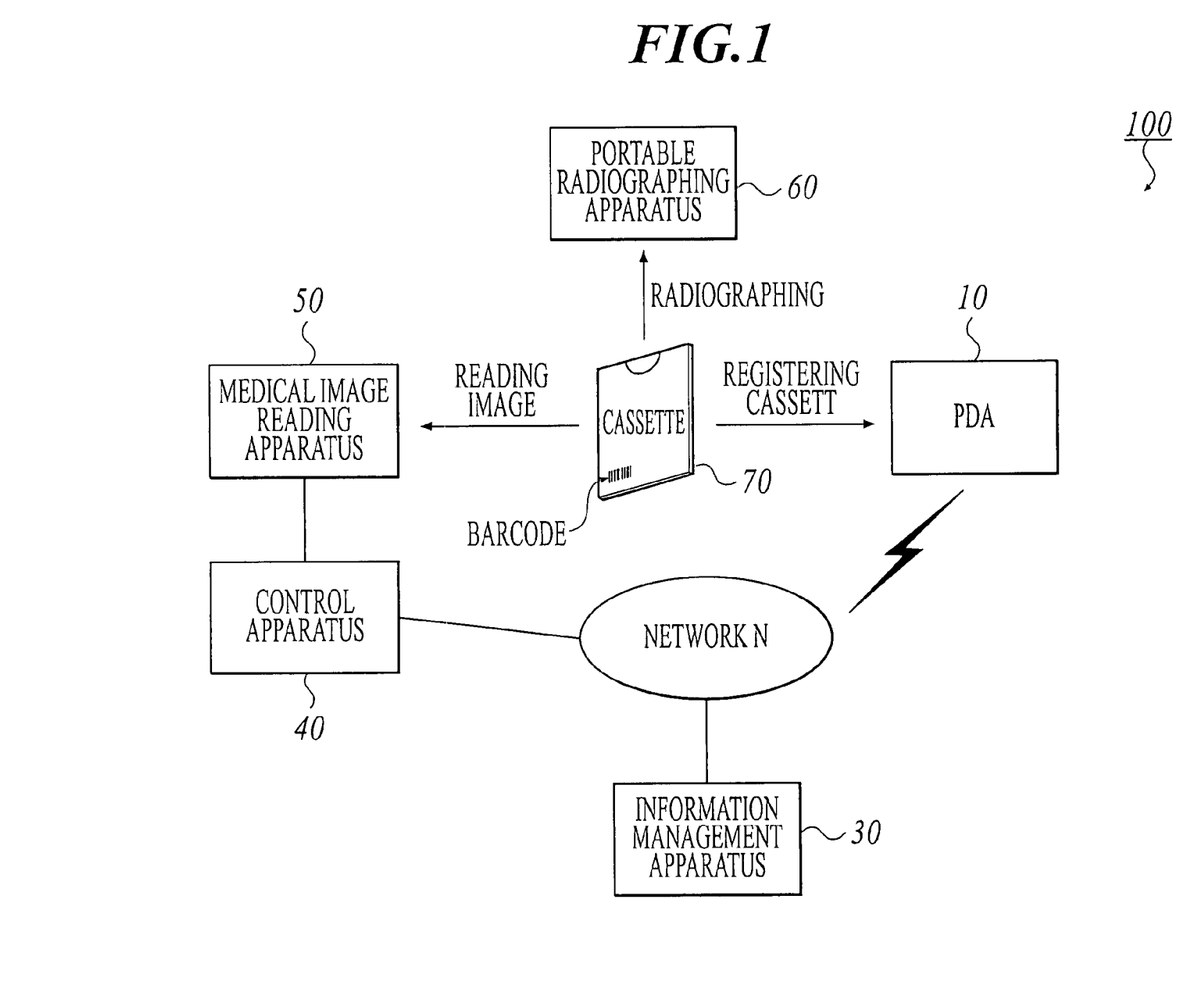
FIG. 1 is a conceptual view showing the whole configuration of a medical image radiographing system according to the embodiment of the present invention.

FIG. 1 is a conceptual view showing the whole configuration of a medical image radiographing system 100 according to the embodiment of the present invention.

In FIG. 1, the medical image radiographing system 100 comprises a portable radiographing information apparatus (hereinafter, named "personal digital assistance (PDA)") 10, a control apparatus 40, a medical image reading apparatus 50 and a portable radiographing apparatus 60. The PDA 10, an information management apparatus 30 and the control apparatus 40 are connected with one another through a network N so as to be able to transmit and receive data to/from one another. The medical image reading apparatus 50 is connected with the control apparatus 40 through a wire. However, the present invention is not limited to this connection, and the medical image reading apparatus 50 may be connected to the network N.

Various networks such as a local area network (LAN), a wide area network (WAN), an internet and the like can be applied to the network N. Further, wireless communication or infrared communication may be applied to the network N on condition that the communication is allowed in a medical institution such as a hospital or the like. However, because radiographing order information includes patient information relating to privacy of the patient, the radiographing order information is enciphered in the transmission and reception of the radiographing order information.

The information management apparatus 30 receives and manages pieces of radiographing order information inputted by a doctor(s) and transmits each piece of radiographing order information to the PDA 10 and the medical image reading apparatus 50 through the network N. A reception apparatus to receive the reservation of a radiographing order and managing the radiographing order information corresponding to the radiographing order may be applied as the information management apparatus, and an information management system such as a hospital information system (HIS), a radiology information system (RIS) or the like may be applied as the information management apparatus.

The PDA 10 comprises a portable radiographing information apparatus which is carried by a radiographer such as a radiographing operator or the like. The PDA 10 receives the pieces of radiographing order information from the information management apparatus 30 and stores the pieces of radiographing order information. In radiographing, the PDA 10 displays specified radiographing order information. In this embodiment, the PDA 10 is applied as the portable radiographing information apparatus. However, a portable note type personal computer, a portable telephone terminal or the like may be applied as the portable radiographing information apparatus.

The portable radiographing apparatus 60 is a movable medical image radiographing apparatus, radiographs each of patients at a visited patient's position according to the operation of a radiographer and records a radiographed medical image of the patient in a cassette 70. The cassette 70 contains a photostimulable phosphor plate and records the radiographed medical image of the patient. A cassette identification number (ID) expressed by a barcode is attached to the surface of the cassette 70 as identification information of the cassette 70.

The medical image reading apparatus 50 is a medical image reading apparatus privately used for the cassette 70 to read out the medical image recorded in the cassette 70. Further the medical image reading apparatus 50 has a barcode reader. In the reading-out of the medical image, the medical image reading apparatus 50 reads out the cassette ID expressed by the barcode and transmits the cassette ID and the medical image to the control apparatus 40 while setting the correspondence of the medical image to the cassette ID.

The cassette 70 of this embodiment is a cassette containing a phosphor plate with a photostimulable phosphor layer formed on a support member. In the radiographing, radiations transmitted through a subject are absorbed in the phosphor layer, and radiation energy corresponding to the radiation transmittance of each part of the subject is accumulated in the phosphor layer. The medical image reading apparatus 50 of this embodiment is a CR apparatus reading out a medical image. In the medical image reading apparatus 50, after the radiographing, the phosphor plate contained in the cassette 70 is scanned by excitation light such as laser light or the like to release the radiation energy accumulated in the phosphor layer as fluorescence, and the fluorescence is converged and photoelectrically converted to read out the medical image.

The control apparatus 40 controls a reading-out operation performed by the medical image reading apparatus 50 and obtains the read-out medical image from the medical image reading apparatus 50. Further the control apparatus 40 receives the radiographing order information from the information management apparatus 30 and sets the correspondence of the medical image to the received radiographing order information to manage the medical image.

The PDA 10 will be described with reference to FIG. 2.

Figure 2:
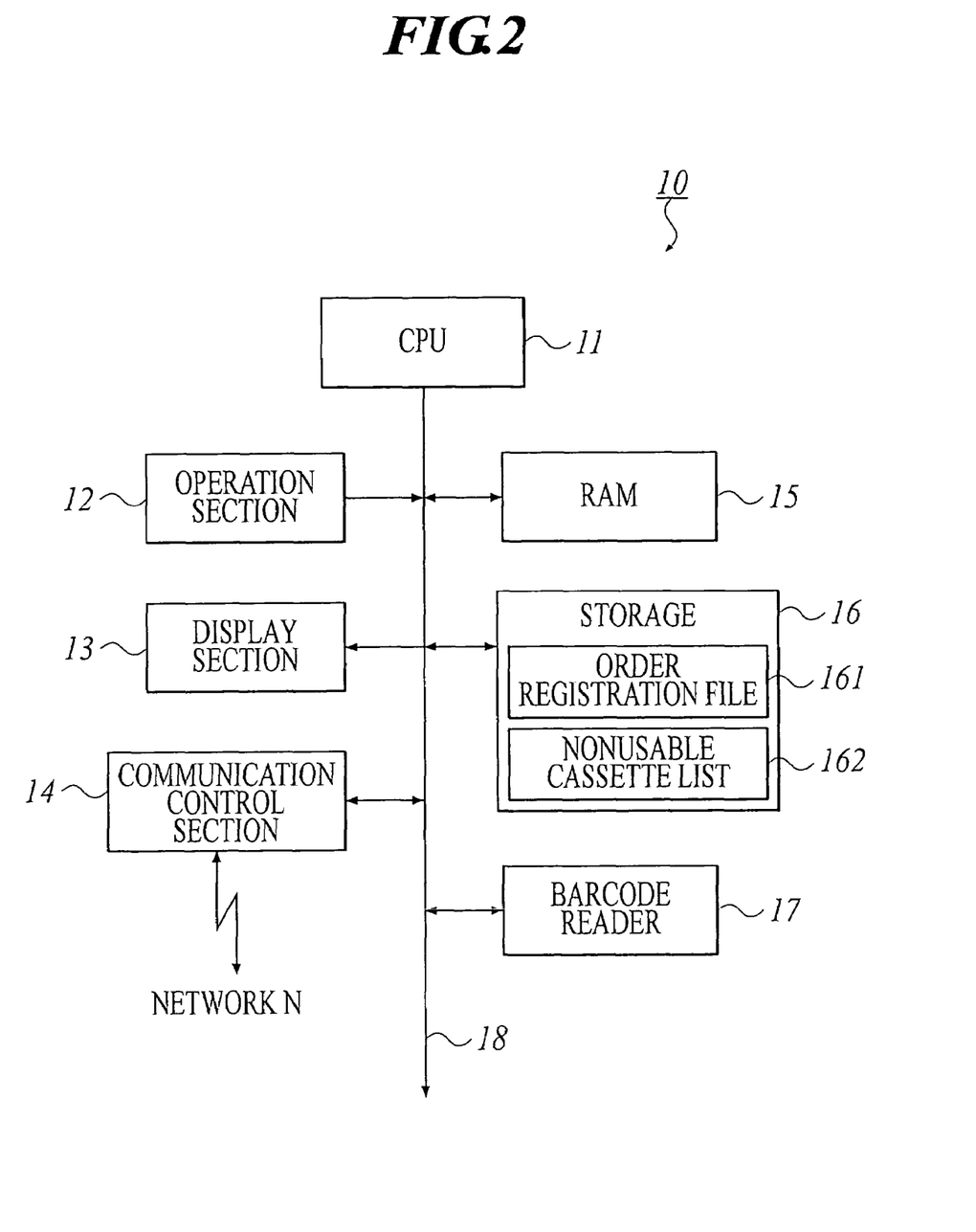
FIG. 2 is a block diagram showing the functional configuration of a portable radiographing information apparatus of FIG. 1.

FIG. 2 is a block diagram showing the functional configuration of the PDA 10 according to this embodiment. In FIG. 2, the PDA 10 comprises a central processing unit (CPU) 11, an operation section 12, a display section 13, a communication control section 14, a random access memory (RAM) 15, a storage 16 and a barcode reader 17. The constituent elements of the PDA 10 are connected with one another through a bus 19.

The CPU 11 expands a program which is designated and selected from a system program and various types of application programs stored in the storage 16 and controls intensively each element of the PDA 10 according to the designated program.

The CPU 11 acts as a correspondence setting section of the PDA 10 by executing each program stored in the storage 16. In detail, the CPU 11 reads out the designated radiographing order information from an order registration file 161 of the storage 16 in response to a request of the radiographer inputted to the operation section 12 and controls the display section 13 to display the designated radiographing order information. When the cassette 70 used for the radiographing is designated by the radiographer, the cassette ID of the designated cassette 70 is inputted to the barcode reader 17, and the inputted cassette ID is stored in the order registration file 161 while setting the correspondence of the inputted cassette ID to the designated radiographing order information. That is, the cassette registration is performed.

After the radiographing, the CPU 11 reads out the radiographing order information already used for the radiographing from the order registration file 161 and transmits the read-out radiographing order information and the cassette ID corresponding to the radiographing order information to the control apparatus 40 through the communication control section 14.

Further, when the CPU 11 receives the cassette ID of the cassette set to be nonusable for next radiographing from the control apparatus 40, the CPU 11 controls the storage 16 to store the cassette ID in an nonusable cassette list 162. In the cassette registration in the next radiographing, when the cassette used for the next radiographing is designated by the radiographer, the CPU 11 controls the barcode reader 17 to read out the cassette ID of the designated cassette 70 and judges whether or not the cassette ID agreeing with the read-out cassette ID is stored in the nonusable cassette list 162. When the cassette ID is stored in the nonusable cassette list 162, the CPU 11 controls the display section 13 to display a warning message indicating that the designated cassette 70 cannot be used for the next radiographing, and the CPU 11 prohibits the cassette registration for the designated cassette 70.

The operation section 12 comprises a cursor key, numeral input keys and various functional keys and outputs a push-down signal corresponding to a pushed-down key. The operation section 12 may further comprise a pointing device such as a touch panel or the like or another input apparatus, if necessary.

The display section 13 is one of warning sections of the control apparatus 40 and comprises a display such as a liquid crystal display (LCD) or the like. When the cassette ID of the cassette 70 desired to be registered agrees with the cassette ID of the cassette 70 judged to be nonusable for the next radiographing, the display section 13 displays a message warning that the cassette 70 desired to be registered is nonusable. A speaker or the like outputting a warning sound may be applied as another warning section. Further, the display section 13 displays various types display data such as the radiographing order information and the like according to a display instruction transmitted from the CPU 11.

The communication control section 14 comprises a network interface card, a modem or a terminal adapter and the like, acts as a radiographing order receiving section and a radiographing order transmitting section and controls the communication with an external apparatus through the network N. For example, the communication control section 14 establishes the wireless communication with the information management apparatus 30 before the radiographing to receive radiographing order information from the information management apparatus 30 and establishes the wireless communication with the control apparatus 40 after the radiographing to transmit the radiographing order information already used for the radiographing and the cassette ID corresponding to the radiographing order information to the control apparatus 40. In this case, if necessary, the wireless communication may be established by using a portable telephone terminal such as Personal Handyphone System (PHS) or the like.

The RAM 15 has a work area for temporarily storing various programs executed by the CPU 11, pieces of data processed according to the programs and the like.

The storage 16 comprises a storage medium (not shown) in which programs and data are stored in advance. The storage medium stores a system program, various application programs corresponding to the system program and data obtained by executing each of various processing programs. The storage medium comprises a magnetic or optical storage medium or a semiconductor memory and is attached to the storage 16 fixedly or detachably.

The storage 16 further comprises the order registration file 161 and the nonusable cassette list 162.

The order registration file 161 acts as a storing section to store the radiographing order information received from the information management apparatus 30 through the communication control section 14.

Figure 3:
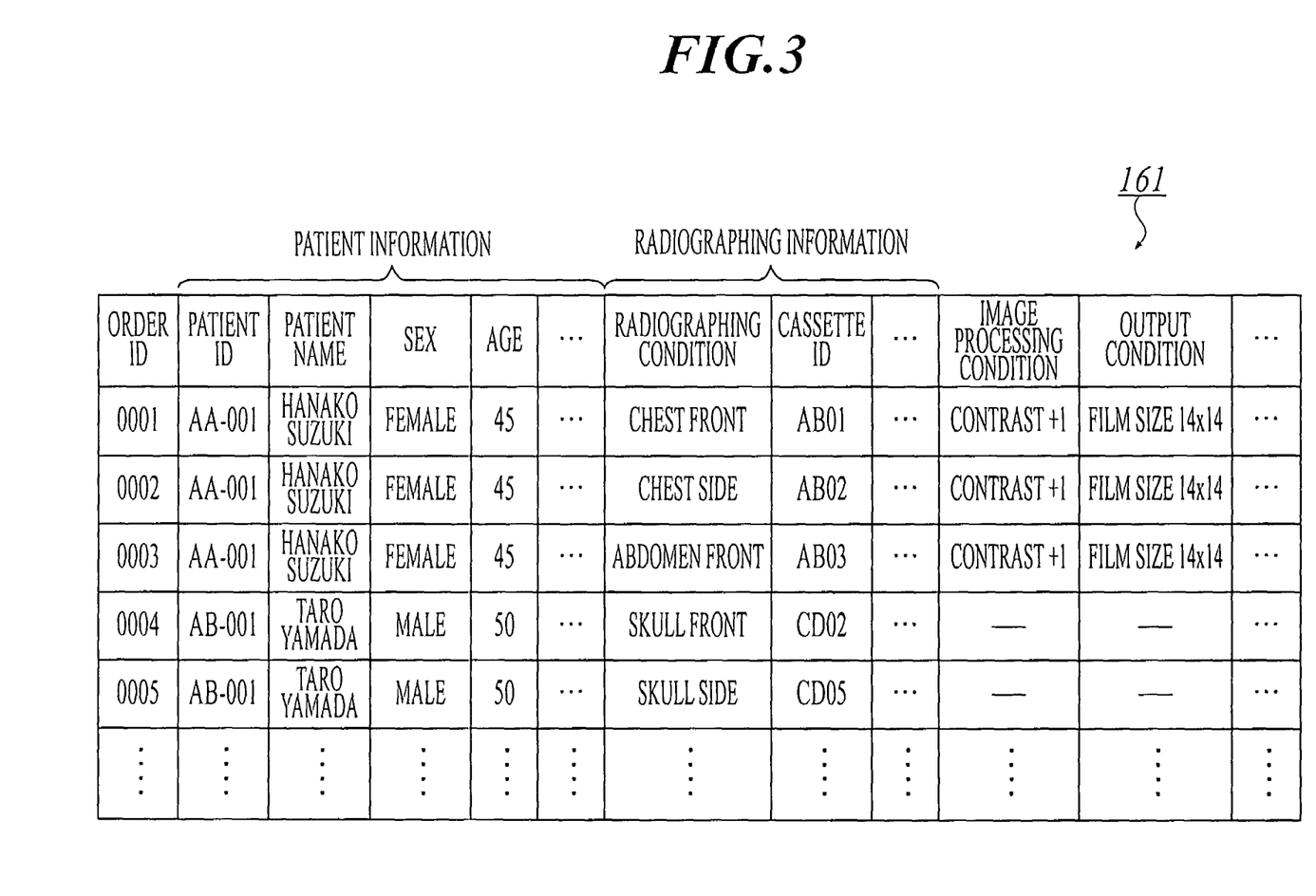
FIG. 3 is a view showing a data storing example of an order registration file stored in a storage of FIG. 2.

A data storing example is shown in FIG. 3. The order registration file 161 stores, in order of the order ID, patient information of each radiographed patient such as an ID (for example, "AA-001"), a name (for example, "SUZUKI Hanako"), a sex (for example, "female" or "male"), an age (for example, "45") and the like, radiographing conditions (including a radiographic part of the patient and a radiographing direction. For example, "front of chest"), radiographing information such as cassette ID (for example, "AB01") of the cassette used for the radiographing and the like, image processing conditions (for example, "contrast +1" indicating the level-up of contrast by one in the gradation processing) of a radiographed medical image, and output conditions (for example, "film size 14×14" indicating a film size in the output of a film) of the radiographed medical image.

The patient information of each patient stored in the file 161 comprises, for example, a department in charge of examination, a name of a doctor in charge, a hospital room, warning information indicating the warning of infectious diseases and the like, the/no existence of a drug allergy, pregnancy or not, an additional clinical history, the/no necessity of special nursing such as the/no necessity of a wheel chair, the/no necessity of a stretcher or the like, a clinically diagnosed disease, privileged information to be protected and the like, in addition to an ID, a name, a sex and an age of the patient shown in FIG. 3.

The radiographing information stored in the file 161 comprises, for example, a radiographing method (simple radiography, contrast radiography or the like), an expected date of the radiographing, a radiographing apparatus, a reader and the like, in addition to the radiographing conditions and the cassette ID shown in FIG. 3.

Image processing conditions in various types image processing are stored in the file 161 as the image processing conditions and comprise, for example, a condition of frequency processing to adjust clearness of the image, a condition of dynamic range compressing processing to set the image of a wide dynamic range to an easily-seen density range without lowering the contrast of minute portions of the subject, a condition of compressing processing to compress image data according to a prescribed compressing method and the like, in addition to the image processing condition in the gradation processing.

The output conditions stored in the file 161 comprise, for example, the reversal, rotation, brightness, contrast and the like in the display and output of the radiographed image, in addition to the film size in the output of the film.

The nonusable cassette list 162 stores the cassette ID(s) of the cassette(s) 70 set to the nonusable condition by the control apparatus 40.

The barcode reader 17 is one of input sections of the PDA 10 and comprises a scanner of an optical read-out mechanism. The barcode reader 17 reads out the barcode attached to the cassette 70 and denoting the cassette ID by using the scanner and outputs the barcode to the CPU 11.

The cassette ID may be inputted according to a key manipulation by applying the operation section 12 as another input section. Further the cassette ID may be inputted by attaching the cassette ID expressed by optical character recognition (OCR) characters to the surface of the cassette 70 and by inputting the cassette ID to an input section such as a scanner or the like to read out the OCR characters. Moreover the cassette ID may be inputted by arranging a semiconductor integrated circuit (hereinafter, named "integrated circuit (IC)") on the cassette 70, recording the cassette ID in the IC and reading out the cassette ID with an IC reader used as an input section.

The control apparatus 40 will be described with reference to FIG. 4.

Figure 4:
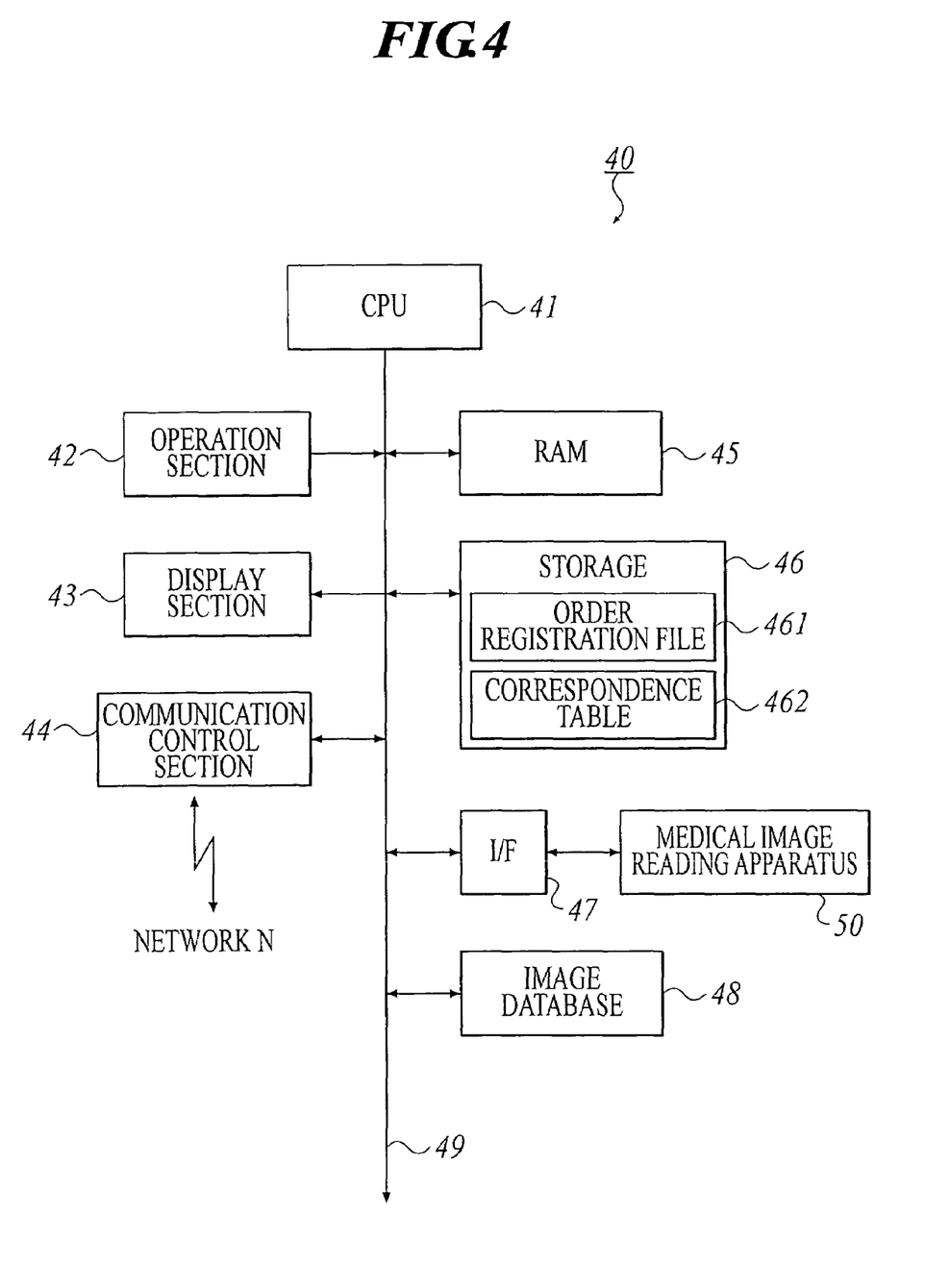
FIG. 4 is a block diagram showing the functional configuration of a control apparatus of FIG. 1.

FIG. 4 is a block diagram showing the functional configuration of the control apparatus 40. In FIG. 4, the control apparatus 40 comprises a central processing unit (CPU) 41, an operation section 42, a display section 43, a communication control section 44, an RAM 45, a storage 46, an interface (I/F) 47 and an image database 48. The elements of the control apparatus 40 are connected with one another though a bus 49. Detailed description of constituent elements (that is, the operation section 42, the display section 43 and the RAM 45) of the control apparatus 40 having the same functions as those of the PDA 10 is omitted.

The CPU 41 expands a program, which is designated and selected from a system program and various types of application programs stored in the storage 46, in the RAM 45 and controls intensively each element of the control apparatus 40 according to the designated program.

In detail, the CPU 41 acts as a judging section of the control apparatus 40 by reading out a cassette judging processing program from the storage 46 and executing the program.

When the CPU 41 receives both the radiographing order information already used for the radiographing and the cassette ID registered in the radiographing order information from the PDA 10 in the cassette judging processing (refer to FIG. 7), the correspondence of the cassette 70 to the radiographing order information is set in a correspondence table (image correspondence setting section) 462 of the storage 46. Thereafter, when the CPU 41 obtains the medical image read out from the radiographed cassette 70 and the cassette ID of the radiographed cassette 70, the correspondence of the medical image to the cassette 70 is set in the correspondence table 462. After the reading-out of medical images from all cassettes 70 is completed, the CPU 41 refers to the correspondence table 462 and judges whether or not medical images are read out from all cassettes 70 respectively, that is, each cassette 70 used for the current radiographing can be used for next radiographing.

When the CPU 41 judges that the medical image of one cassette 70 is not yet read out, the cassette 70 is set to the nonusable condition in the correspondence table 462. In contrast, when the CPU 41 judges that the medical image of one cassette 70 has been already read out, the cassette 70 is set to the usable condition in the correspondence table 462. The CPU 41 then controls the PDA 10 to transmit judging results indicating usable or nonusable cassettes 70 in next radiographing to the communication control section 44.

The communication control section 44 comprises a network interface card, a modem or a terminal adapter and the like, acts as a judging result transmitting section and controls the communication with an external apparatus through the network N. For example, the communication control section 44 transmits the judging results of the usable or nonusable cassettes 70 obtained due to the cooperation of the CPU 41 and the cassette judging processing program to the PDA 10. Further the communication control section 44 receives the radiographing order information from the information management apparatus 30 before the radiographing and receives the radiographing order information already used for the radiographing and the cassette ID registered in the radiographing order information from the PDA 10 after the radiographing.

The storage 46 comprises a storage medium (not shown) in which programs and data are stored in advance. The storage medium stores a system program, various application programs corresponding to the system program and data obtained by executing each of various processing programs. The storage medium comprises a magnetic or optical storage medium or a semiconductor memory and is attached to the storage 46 fixedly or detachably.

The storage 46 stores an order registration file 461 and a correspondence table 462.

The order registration file 461 registers the radiographing order information received from the information management apparatus 30 and functions in the same manner as the order registration file 161. Therefore, detailed description of the order registration file 461 is omitted.

Figure 5:
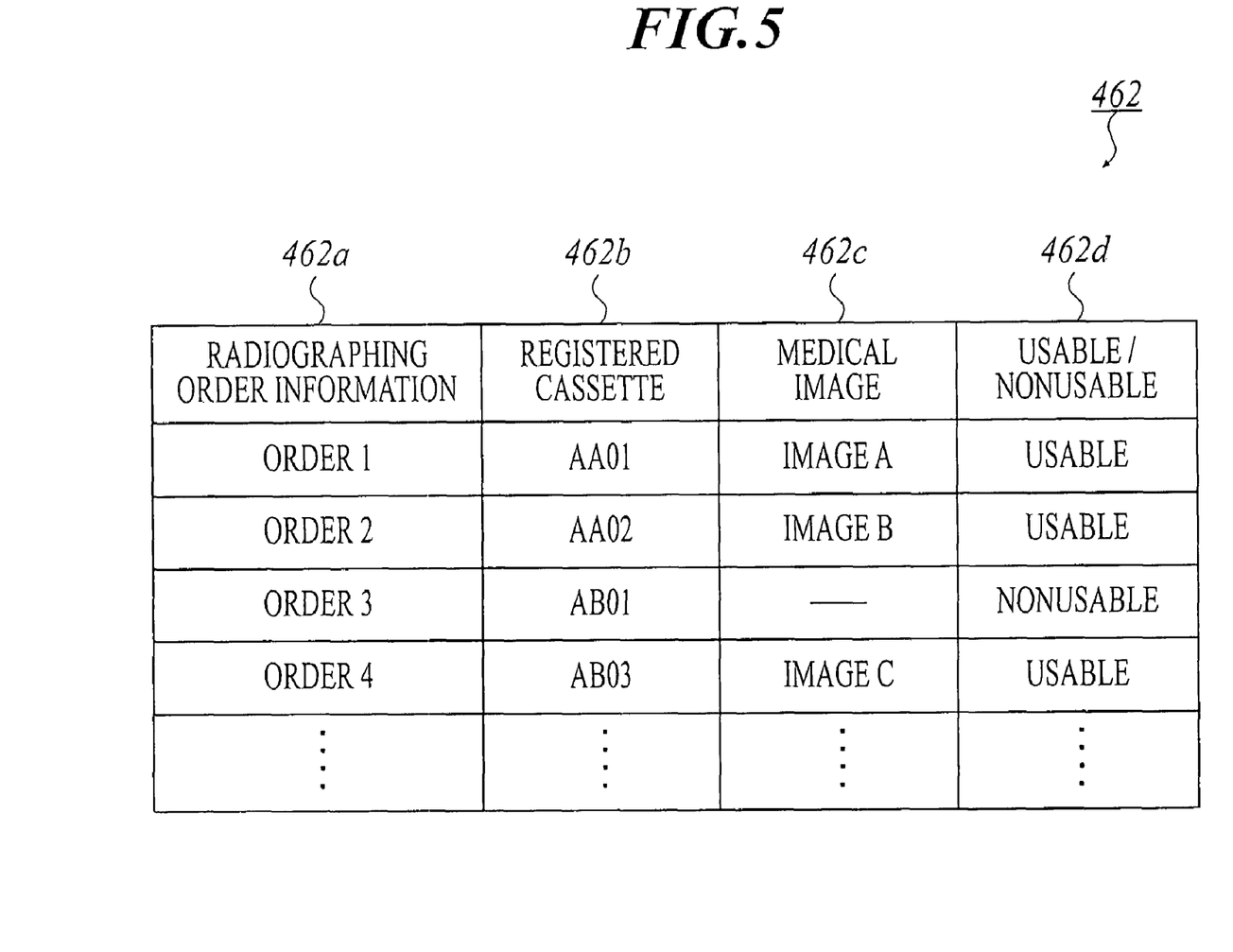
FIG. 5 is a view showing a data storing example of a correspondence table stored in a storage of FIG. 3.

As a data storing example is shown in FIG. 5, the correspondence table 462 has columns of radiographing order information 462a, registered cassette 462b, medical image 462c and usable/nonusable state 462d for next radiographing and stores the radiographing order information corresponding to one radiographed cassette 70, the cassette ID of the cassette 70 registered in the radiographing order information by the PDA 10, information of the medical image read out from the cassette 70 and the setting of a usable or nonusable condition for next radiographing respectively registered in the columns 462a to 462d while setting the correspondence of the data of the columns 462a to 462d to one another. For example, the cassette ID of the cassette 70 registered in the radiographing order information of "order 1" is expressed by "AA01", the medical image read out from the cassette 70 is expressed by "image A", and the cassette 70 usable for next radiographing is expressed by "usable"

The I/F 47 is an interface to connect the control apparatus 40 to the medical image reading apparatus 50 and receives both the medical image and the cassette ID of the cassette 70 recording the medical image from the medical image reading apparatus 50 after the radiographing. The received medical image is output to the image database 48 under the control of the CPU 41.

The image database 48 stores data of the medical image received from the medical image reading apparatus 50, and the stored data can be read out in response to a request from the outside.

Next, an operation in this embodiment will be described.

The programs embodying functions described in flow charts described later are stored in the storage 16 of the PDA 10 or the storage 46 of the control apparatus 40 in the form of a program code readable by a computer, and the storage 16 of the PDA 10 and the storage 46 of the control apparatus 40 perform the operations one after another according to the program code.

The whole flow of the radiographing in the medical image radiographing system 100 will be initially described with reference to FIG. 6.

Figure 6:
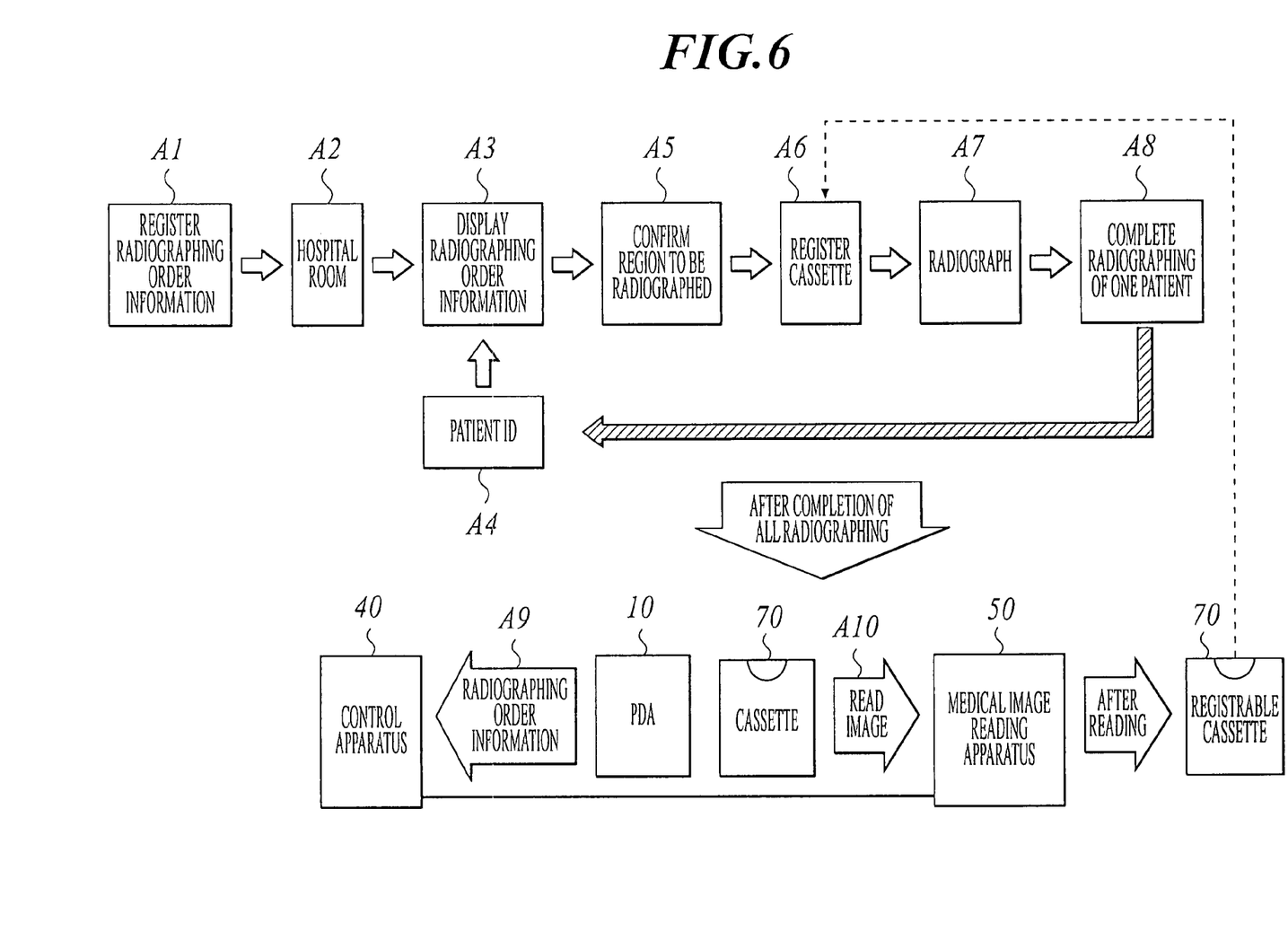
FIG. 6 is a view explaining the whole flow of the radiographing in the medical image radiographing system of FIG. 1.

In FIG. 6, the information management apparatus 30 initially transmits the radiographing order information to the PDA 10. The PDA 10 stores and registers the radiographing order information received from the information management apparatus 30 in the order registration file 161 (step A1).

The radiographer then carries the portable radiographing apparatus 50 and the cassette 70 to the hospital room of the patient and starts preparing the radiographing (step A2). When the preparation of the radiographing is completed, the radiographer operates the PDA 10 to instruct the display section 13 of pieces of radiographing order information. The PDA 10 then displays a list of the pieces of radiographing order information (step A3) in response to the instruction of the display of the pieces of radiographing order information. Thereafter, when the radiographer inputs the patient ID of the patient to be radiographed to the PDA 10 (step A4), the PDA 10 displays the radiographing order information corresponding to the inputted patient ID (step A3). When there are pieces of radiographing order information corresponding to the inputted patient ID, the radiographer selects and designates the desired radiographing order information from the pieces of displayed radiographing order information.

When the radiographer confirms the radiographic part of the radiographing order information displayed on the PDA 10 (step A5), the radiographer registers the cassette 70 used for the radiographing (step A6). In detail, the radiographer then designates the cassette 70 used for the radiographing and uses the barcode reader 17 of the PDA 10 to read out the barcode indicating the cassette ID of the cassette 70. The PDA 10 then registers the read-out cassette ID to the order registration file 161 while setting the correspondence of the cassette ID to the designated radiographing order information. Therefore, the cassette registration is completed.

The radiographer then radiographs the patient with X-rays according to the radiographing order information displayed on the PDA 10 by using the registered cassette 70 and the potable radiographing apparatus 50 (step A7). When the radiographing for one patient according to one piece of radiographing order information or a plurality of pieces of radiographing order information is completed (step A8), the radiographer inputs a patient ID of a next patient to be radiographed (step A4) and performs a series of radiographing operations for the next patient in the same manner.

After the radiographing of all patients, that is, after the completion of the radiographing according to all pieces of radiographing order information registered in the order registration file 161 of the PDA 10, the PDA 10 transmits the pieces of radiographing order information and the cassette IDs corresponding to the pieces of radiographing order information to the control apparatus 40 to inform the control apparatus 40 of the cassette 70 used for the radiographing according to each piece of radiographing order information (step A9). Further the radiographer attaches each cassette 70 to the medical image reading apparatus 50 and instructs the apparatus 50 to read out the medical image recorded in the cassette 70. The medical image reading apparatus 50 then reads out the medical image and the cassette ID from the cassette 70 (step A10). When the medical image reading apparatus 50 reads out the medical image and the cassette ID, the medical image reading apparatus 50 transmits the medical image and the cassette ID to the control apparatus 40 while setting the correspondence of the medical image to the cassette ID.

The control apparatus 40 then performs cassette judging processing described later according to pieces of information received from the medical image reading apparatus 50 to judge whether or not each cassette used for the current radiographing is usable for next radiographing, and the control apparatus 40 transmits judging results to the PDA 10. The PDA 10 sets only the cassette(s) 70 judged to be usable for the next radiographing to the usable condition.

Next, the cassette judging processing performed by the CPU 41 of the control apparatus 40 will be described with reference to FIG. 7.

Figure 7:
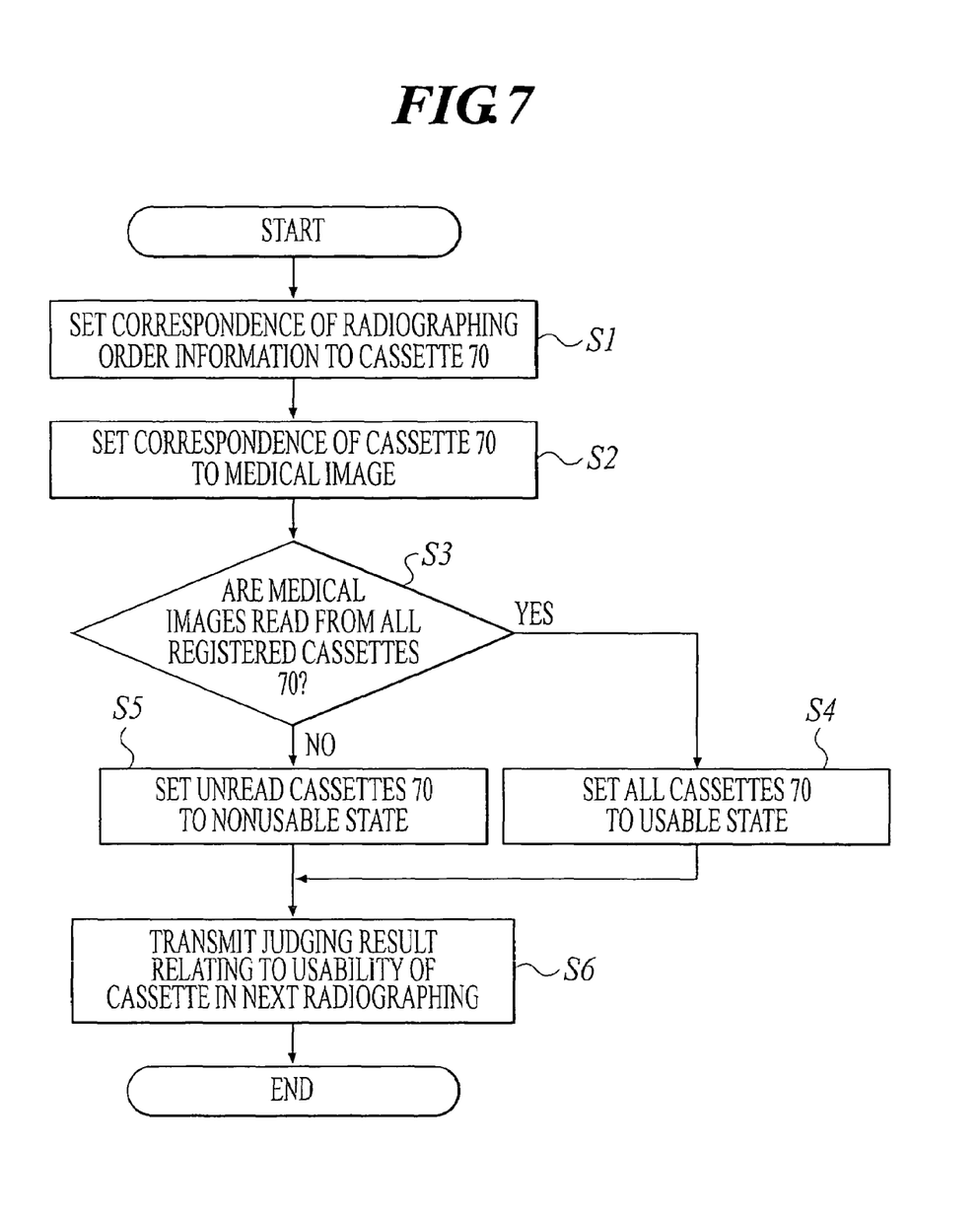
FIG. 7 is a flow chart explaining cassette judging processing performed by the portable radiographing information apparatus and the control apparatus.

In FIG. 7, the CPU 41 registers the pieces of radiographing order information already used for the radiographing and received from the PDA 10 one after another in the column of radiographing order information 462a of the correspondence table 462, simultaneously registers the cassette ID corresponding to each piece of radiographing order information in the column of the registered cassette 462b while setting the correspondence of the cassette ID to the radiographing order information. Therefore, the CPU 41 sets the correspondence of each cassette 70 to the radiographing order information (step S1).

When the CPU 41 then receives each of the medical images and the cassette ID of the cassette 70 recording the medical image from the medical image reading apparatus 50, the CPU 41 collates the received cassette ID with each cassette ID listed in the column of the registered cassette 462b of the correspondence table 462 and registers information of the received medical image to the row of the column of the medical image 462c corresponding to the listed cassette ID agreeing with the received cassette ID. Therefore, the CPU 41 sets the correspondence of each medical image to the registered cassette 70 (step S2).

When the reading-out of the medical images from all cassettes 70 used for the radiographing and the setting of the correspondence in the correspondence table 462 are completed, the CPU 41 refers to the correspondence table 462 to search the column of the medical image 462c for a row(s) not listing information of the medical image, and the CPU 41 judges whether or not the medical images are read out from all registered cassettes 70, that is, all cassettes 70 used for the current radiographing are usable for next radiographing (step S3). For example, when the radiographer erroneously forgets to attach one cassette 70 to the medical image reading apparatus 50, no medical image is read out from the cassette 70. Therefore, there is a row of the column of the medical image 462c not listing information of the medical image.

When information of the medical image is listed in all rows of the column of the medical image 462c and the medical images are read out from all registered cassettes 70, the CPU 41 judges that all cassettes 70 used for the current radiographing are usable for next radiographing and sets all rows of the column of the usable/nonusable state 462d to "usable" (step S4) to set all cassettes 70 to the usable state. Thereafter, the procedure proceeds to a step S6.

In contrast, when there is/are a row(s) not listing information of the medical image in the column of the medical image 462c and there is/are a cassette(s) 70 recording unread medical image(s), the CPU 41 sets the row(s) of the column of the usable/nonusable state 462d of the correspondence table 462 to "nonusable", and the CPU 41 sets the row(s) listing the medical image(s) in the column of the usable/nonusable state 462d to the "usable" state (step S5). For example, as shown in FIG. 5, because no information of medical image is listed in the row of the column of the medical image 462c corresponding to "order 3" of the radiographing order information 462a, the CPU 41 sets the row of the column of the usable/nonusable state 462d to "nonusable" and sets the rows of the column of the usable/nonusable state 462d, in which the medical images are listed in the column of the medical image 462c, to "usable".

When the CPU 41 then obtains the cassette ID(s) set to "nonusable" and the cassette ID(s) set to "usable" from the column of the registration cassette 462d, the CPU 41 transmits each obtained cassette ID to the PDA 10 as the judging result relating to usability in next radiographing (step S6), and the CPU 41 completes the cassette judging processing.

When the PDA 10 judges according to the judging result received from the control apparatus 40 that the PDA 10 receives the cassette ID of "nonusable", the PDA 10 registers the cassette ID in the nonusable cassette list 162. Thereafter, in the cassette registration for next radiographing, the cassette ID of each cassette 70 to be registered is read out by the barcode reader 17, and the PDA 10 judges whether or not the cassette ID agreeing with the read-out cassette ID is listed in the nonusable cassette list 162.

When the PDA 10 judges that the cassette ID agreeing with the read-out cassette ID is listed in the nonusable cassette list 162, the PDA 10 displays a warning message "this cassette has an unread image and is nonusable" or the like on the display section 13 to warn that the cassette 70 to be registered is nonusable for radiographing, and the PDA 10 prohibits the registration of the cassette 70.

Further, when the medical image is read out from the cassette 70 set in "nonusable" by the medical image reading apparatus 50 and the cassette 70 is set to "usable" by the control apparatus 40, the control apparatus 40 controls the communication control section 44 to transmit the cassette ID of the cassette 70 set to "usable" to the PDA 10. When the PDA 10 judges that the cassette ID agreeing with the received cassette ID of "usable" is listed in the nonusable cassette list 162, the listed cassette ID is deleted from the nonusable cassette list 162.

As described above, because the plurality of pieces of radiographing order information are registered and displayed in the PDA 10 brought with the radiographer, the handling of the pieces of radiographing order information can be made easy and accurate, and the desired piece of radiographing order information can be easily distinguished from the other pieces of radiographing order information. Accordingly, the burden of the radiographer for the radiographing operation can be mitigated.

Further, according to both the radiographing order information used for the radiographing and the cassette ID corresponding to the radiographing order information transmitted from the PDA 10 and both the medical image and the cassette ID of the cassette 70 recording the medical image obtained from the medical image reading apparatus 50, the control apparatus 40 judges whether or not the cassette 70 used for the radiographing is usable for next radiographing, and the PDA 10 receives the judging result from the control apparatus 40 and prohibits the cassette 70 judged to be nonusable from being registered for next radiographing. Accordingly, the duplicated radiographing for the cassette 70, from which no medical image is read out, can be prevented.

Moreover, even though the cassette 70 is once set to "nonusable", the setting of the cassette 70 set to "nonusable" is changed to "usable" by making the medical image reading apparatus 50 read out the medical image from the cassette 70, and the cassette ID of the cassette 70 changed to "usable" in the PDA 10 is deleted from the nonusable cassette list 162. Accordingly, the setting of "nonusable" can be automatically cancelled, and the burden of the radiographer for the cassette registration operation can be mitigated.

In this embodiment, the cassette 70 is a cassette containing a phosphor plate with a photostimulable phosphor layer formed on a support member, and the medical image reading apparatus 50 is a CR apparatus. However, the present invention is not limited to this. For example, a cassette contains a flat panel detector (FPD) and a memory to store a plurality of medical images obtained in the flat panel detector, a medical image reading apparatus comprises a cradle to receive the medical images from the cassette and a barcode reader to read out identification information of the cassette. In this case, to prevent an amount of data of the medical images of the cassette obtained in the radiographing from being exceeding a capacity of the memory, when a prescribed condition (for example, the number of medical images currently stored in the memory after reading out medical images of the cassette at the previous time is larger than a predetermined number) is satisfied, it is judged that the cassette is nonusable for next radiographing. Of course, the present invention is not limited to the example described above.

The entire disclosure of Japanese Patent Application No. Tokugan 2002-317451 filed on Oct. 31, 2002 including specification, claims, drawings and summary are incorporated herein by reference in its entirety.

What is claimed is:

1. A medical image radiographing system for radiographing each of patients at a visited patient's location, the system comprising:
a medical image reading apparatus to read out identification information of a cassette and a medical image converted from radiation energy absorbed in a phosphor plate contained in the cassette according to radiographing order information;
a portable radiographing information apparatus displaying previously stored radiographing order information at the visited patient's location, the apparatus having a correspondence setting section to set correspondence of the identification information of the cassette to the radiographing order information for radiographing using the cassette; and
a judging section to judge whether the medical image recorded in the phosphor plate contained in the cassette is read by the medical image reading apparatus,
wherein the correspondence setting section prohibits the setting of the correspondence of the identification information of the cassette, when the cassette is judged as the medical image is not read by the medical image reading apparatus by the judging section.

2. The medical image radiographing system of claim 1; further comprising:
a control apparatus to control the medical image reading apparatus to obtain the identification information and the medical image of the cassette,
the control apparatus comprising:
the judging section; and
a judging result transmitting section to transmit a judging result obtained by the judging section to the portable radiographing information apparatus,
wherein the correspondence setting section of the portable radiographing information apparatus prohibits the setting of the correspondence according to the judging result transmitted from the judging result transmitting section.

3. The medical image radiographing system of claim 1; wherein the portable radiographing information apparatus further comprises:
a radiographing order receiving section to receive one or more pieces of radiographing order information;
a storing section to store the one or more pieces of radiographing order information received by the radiographing order receiving section;
an input section to input the identification information of the cassette used for radiographing in; and
a radiographing order transmitting section to transmit the identification information of the cassette and the radiographing order information, of which the correspondence to each other is set by the correspondence setting section, to the control apparatus after the radiographing, wherein the correspondence setting section of the portable radiographing information apparatus sets the correspondence of the identification information of the cassette inputted by the input section to one piece of radiographing order information which is selected from the one or more pieces of radiographing order information stored by the storing section and which relates to the radiographing using the cassette, and wherein the judging section judges whether or not the cassette is usable for the next radiographing, according to both the identification information of the cassette and the radiographing order information transmitted by the radiographing order transmitting section and both the identification information of the cassette and the medical image obtained by the medical image reading apparatus.

4. The medical image radiographing system of claim 2; wherein the control apparatus and the portable radiographing information apparatus are connected with each other through a network, and the medical image reading apparatus and the control apparatus are connected with each other through a wire.

5. The medical image radiographing system of claim 2; wherein the control apparatus, the portable radiographing information apparatus and the medical image reading apparatus are connected with one another through a network.

6. The medical image radiographing system of claim 3; wherein the portable radiographing information apparatus further comprises a warning section to warn that the cassette is nonusable when the identification information of the cassette inputted by the input section agrees with the identification information of the cassette judged to be nonusable for the next radiographing, according to a judging result of the judging section.

7. The medical image radiographing system of claim 1; wherein the medical image reading apparatus sets the correspondence of the identification information of the cassette to the medical image read out from the cassette, the system further comprising:
an image correspondence setting section to set the correspondence of the medical image to the radiographing order information according to both the identification information of the cassette and the radiographing order information of which the correspondence to each other is set by the correspondence setting section and both the identification information of the cassette and the medical image of which the correspondence to each other is set by the medical image reading apparatus.

8. The medical image radiographing system of claim 2; wherein the medical image reading apparatus sets the correspondence of the identification information of the cassette to the medical image read out from the cassette, and the control apparatus further comprises:
an image correspondence setting section to set the correspondence of the medical image to the radiographing order information according to both the identification information of the cassette and the radiographing order information of which the correspondence to each other is set by the correspondence setting section and both the identification information of the cassette and the medical image of which the correspondence to each other is set by the medical image reading apparatus.

9. A portable radiographing information apparatus for radiographing each of patients at a visited patient's location, which is connected with a medical image reading apparatus to read out identification information of a cassette and a medical image converted from radiation energy absorbed in a phosphor plate contained in the cassette according to radiographing order information, the portable radiographing information apparatus comprising:
a radiographing order information receiving section to receive one or more pieces of radiographing order information;
a storing section to store the one or more pieces of radiographing order information received by the radiographing order information receiving section;
an input section to input the identification information of the cassette used for radiographing in;
a correspondence setting section to set correspondence of the identification information of the cassette inputted by the input section to one piece of radiographing order information which is selected from the one or more pieces of radiographing order information stored by the storing section and which relates to the radiographing using the cassette; and
a radiographing order transmitting section to transmit the identification information of the cassette and the radiographing order information of which the correspondence to each other is set by the correspondence setting section,
wherein the correspondence setting section prohibits the setting of the correspondence of the piece of identification information of the cassette to the radiographing order information of the cassette used for the next radiographing when the cassette is judged as the medical image recorded in the phosphor plate contained in the cassette is not read.

10. The portable radiographing information apparatus of claim 9; further comprising a warning section to warn that the cassette is nonusable when the identification information of the cassette inputted by the input section agrees with the identification information of the cassette judged to be nonusable for the next radiographing.

11. The portable radio graphing information apparatus of claim 10; which is connected with the medical image reading apparatus through a control apparatus.

12. The portable radiographing information apparatus of claim 10; which is connected with the medical image reading apparatus through a network.

* * * * *